United States Patent [19]

Renner et al.

[11] 4,374,986
[45] Feb. 22, 1983

[54] SELECTED SILOXANE ADDUCTS OF TRIS(2-HYDROXYETHYL)ISOCYANURATE

[75] Inventors: Jacqueline M. Renner, New Haven; Robert N. Scott, Wallingford; David F. Gavin, Cheshire, all of Conn.

[73] Assignee: Olin Corporation, New Haven, Conn.

[21] Appl. No.: 289,667

[22] Filed: Aug. 3, 1981

[51] Int. Cl.³ .......................................... C07D 251/34
[52] U.S. Cl. ....................................................... 544/221
[58] Field of Search ........................................ 544/221

[56] References Cited

U.S. PATENT DOCUMENTS

| | | | |
|---|---|---|---|
| 3,088,948 | 5/1963 | Little | 260/248 |
| 3,494,951 | 2/1970 | Berger | 260/448.2 |
| 3,646,090 | 2/1972 | Bennett | 260/448.2 |
| 3,821,218 | 6/1974 | Berger | 260/248 |
| 3,892,643 | 7/1975 | Tanaka | 204/159.13 |
| 3,896,123 | 7/1975 | DeZuba | 260/248 |

FOREIGN PATENT DOCUMENTS 45-34823 11/1970 Japan .

OTHER PUBLICATIONS

Tanaka et al., *Chemical Abstracts*, vol. 74, 76515v, (1971).
Rev. Roumaine Chim. 11(7), pp. 897–899, (1966).
Makromolekulare Chemie, vol. 55, pp. 87–95, (1962).

*Primary Examiner*—John M. Ford
*Attorney, Agent, or Firm*—William A. Simons; Thomas P. O'Day

[57] ABSTRACT

Described are selected siloxane adducts of tris(2-hydroxyethyl)isocyanurate having the formula:

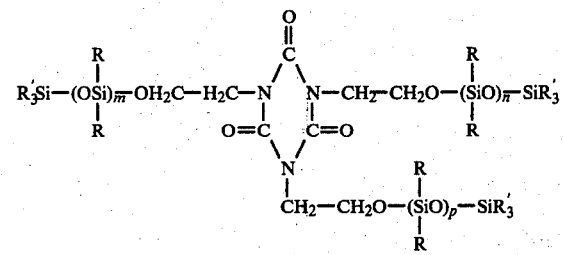

wherein each R and R' is individually selected from lower alkyl groups having 1 to 4 carbon atoms and lower alkoxy groups having 1 to 4 carbon atoms; and the sum of m, n, and p is from 0 to about 20; with the proviso that each R' is a lower alkoxy group when the sum of m, n, and p is 0. These siloxane adducts are also described as good functional fluids, particularly as lubricants and lubricant additives.

6 Claims, No Drawings

SELECTED SILOXANE ADDUCTS OF TRIS(2-HYDROXYETHYL)ISOCYANURATE

BACKGROUND OF THE INVENTION

1. Field of the Invention

This invention relates to selected siloxane adducts of tris(2-hydroxyethyl)isocyanurate as novel compositions of matter. Furthermore, this invention relates to the use of these adducts in functional fluids.

2. Description of the Prior Art

In functional fluid formulations, silicones have the desirable properties of good thermal stability and low temperature resistance. However, a major drawback of silicones is their poor steel-on-steel lubrication. This drawback is inherent even in silicones having relatively high molecular weights and viscosity.

It has now been found that the reaction products of selected silicone functionalities ("siloxane adducts") with a compound having an isocyanurate ring structure, namely, tris(2-hydroxyethyl)isocyanurate, results in a class of compounds having a combination of desirable functional fluid characteristics including good steel-on-steel lubricity.

BRIEF SUMMARY OF THE INVENTION

The present invention is accordingly directed to novel siloxane adducts of tris(2-hydroxyethyl)isocyanurate of the formula (I):

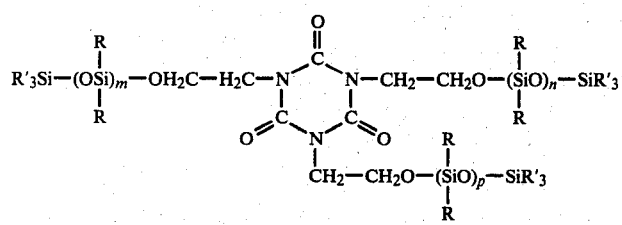

wherein each R and R' are individually selected from lower alkyl groups having 1 to 4 carbon atoms and lower alkoxy groups having 1 to 4 carbon atoms; and the sum of m, n and p is from 0 to about 20; with the proviso that each R' is an alkoxy group when the sum of m, n, and p is 0.

The present invention is also directed to the use of the compounds of formula (I) as functional fluids, particularly as hydraulic fluids.

DETAILED DESCRIPTION

The siloxane adducts of the present invention may be prepared by reacting 3 moles of the corresponding chlorosiloxane with 1 mole of tris(2-hydroxyethyl)isocyanurate (sometimes hereafter referred to as THEIC, preferably in the presence of a suitable solvent like toluene and an acid scavenger like pyridine under atmospheric conditions. This general reaction is illustrated by the following equation (A) wherein 1 mole of THEIC is reacted with 3 moles of 1-chloro-1,1-dimethyl-3,3,3-(tri-sec-butoxy)disiloxane to form tris[2-[4,4-dimethyl-6,6,6-tri(sec-butoxy)]disiloxyethyl]isocyanurate:

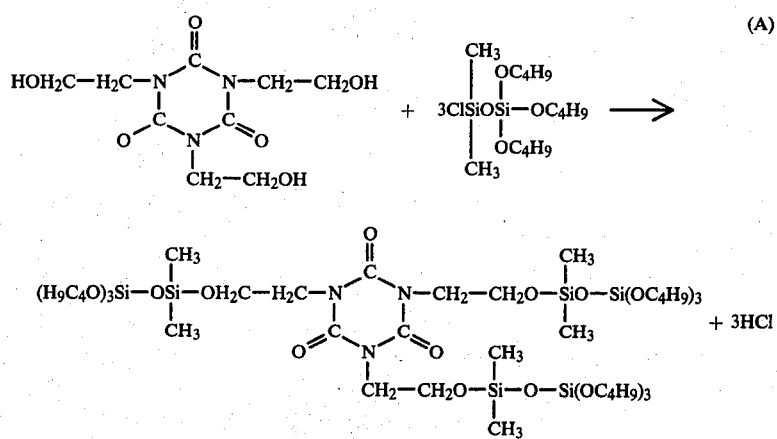

In the reaction illustrated by Equation (A), THEIC is employed as a starting material for making the adducts of the present invention. This chemical compound is commercially available from several sources. One method for making THEIC is taught in U.S. Pat. No. 3,088,948, which issued to Little et al on May 7, 1963.

The other class of reactants of the reaction illustrated by Equation (A) are the corresponding chlorosiloxanes. These precursors are also well known chemicals and may be made by several methods. Specific methods for their synthesis are taught by U.S. Pat. No. 3,646,090, which issued to Bennett on Feb. 29, 1972; by *Rev. Roumaine Chim.*, 11(7), pages 897–899 (1966); and by *Makromolecular Chemie.* Vol. 55, pages 87 to 95 (1962).

The preferred chlorosiloxane reactants would have R' radicals which are all the same. More preferably, all of the R' radicals would be the same lower alkyl or alkoxy groups. Most preferably, all of the R' radicals would be sec-butoxy groups [—OC₄H₉(sec)]. With respect to the R radicals, it is preferred that all of the R radicals be the same lower alkyl or lower alkoxy group. Particularly suitable R radicals are methyl groups (—CH₃) and sec-butoxy groups (—OC₄H₉(sec)). The latter group is favored because of its good lubricity and good hydrolytic stability properties. Preferably, the sum of m, n, and p is from 0 to about 12, more preferably 0 to about 9, while subject to the above proviso.

Representative chlorosiloxane reactants include the following:

trimethylchlorosilane
tri-secbutoxychlorosilane
1-chloro-1,1, dimethyl-3,3,3-trisecbutoxydisiloxane
1-chloro-1,1,3,3-tetramethyl-5,5,5-trisecbutoxytrisiloxane
1-chloro-1,1,3,3,5,5-hexamethyl-7,7,7-trisecbutoxytetrasiloxane
1-chloro-1,1,3,3,5,5,7,7-octamethyl-9,9,9-trisecbutoxypentasiloxane
1-chloro-1,1,3,3,3-pentamethyldisiloxane
1-chloro-1,1,3,3,5,5,5-heptamethyltrisiloxane
1-chloro-1,1,3,3,5,5,7,7,7-nonamethyltetrasiloxane
1-chloro-1,1,-disecbutoxy-3,3,3-trimethyldisiloxane The compounds of this invention are preferably made by reacting about 2.5 to about 3.5 moles of the corresponding chlorosiloxane compound per one mole of THEIC. It is more preferred to employ mole ratios in the range of from about 2.75:1 to about 3.25:1. Most preferably, mole ratios in the range of 2.75:1 to 3.05:1 may be used. Although mole ratios of less than about 2.5:1 may be used, substantially lower yields of the desired product will be produced. Mole ratios above about 3.5:1 may also be employed, but no advantage is seen. The reactants may be added over a period of time.

The reaction of THEIC and the corresponding chlorosiloxane may be preferably carried out at temperatures in the range from about 0° C. to about 100° C., more preferably from about 20° C. to about 90° C. When reaction temperatures are below about 10° C., the reaction times are too slow to be practical. Further, when temperatures are above about 100° C., the possibility of side reactions and product decomposition is increased.

This reaction may be carried out at any suitable reaction pressure. Generally, atmospheric pressure is preferred.

The reaction may be carried out over a period of time ranging from about ½ hour to 20 hours, with the required time decreasing as the reaction temperature is raised.

Any inert solvent may be employed for this reaction. Toluene is a preferred solvent. While a solvent is not necessary, it does serve to moderate the rate of reaction. Preferably, solvents are employed in a range from about 2:1 to about 10:1, more preferably about 4:1 to 6:1, molar excess over the THEIC used.

A hydrogen chloride acceptor base may also be employed in the reaction mixture. The acceptor may be any compound which will accept hydrogen chloride and thereby also promote the formation of the desired product. Among the preferred acceptors are nitrogenated tertiary organic compounds having at least 3 carbon atoms; e.g., the lower alkyl and aryl tertiary amines such as triethyl amine, tributyl amine, as well as pyridine, substituted pyridines, N,N'-dimethylaniline, and the like.

In a preferred operation, THEIC is reacted with a chlorosiloxane in a mole ratio of about 3 moles of the chlorosiloxane to 1 mole of THEIC. The reactants are added together at room temperature in a reaction mixture containing toluene as a solvent and pyridine as an acid acceptor. The reaction mixture is heated to about 60° C. to about 100° C. at atmospheric pressure for sufficient time for the reaction to be complete. After that completion, the reaction mixture is cooled and the desired product is recovered from the reaction mixture.

The recovery methods may be any conventional methods for recovering products of this type. Preferably, any solid by-products are first removed by filtration and the organic phase of the resultant filtrate is washed with water, dried and distilled to recover the liquid product.

Of course, the siloxane adducts of the present invention may be synthesized and recovered by other methods and the present invention is not intended to be limited to any particular method for making or recovering these adducts.

The isocyanurate compounds of the present invention have been found to be particularly useful in functional fluid systems.

The functional fluid systems to which the present invention is directed includes hydraulic-type functional fluid systems and heat transfer-type functional fluid systems.

The hydraulic-type fluid systems include any system wherein a mechanical effort is converted to pressure at a first location, the pressure is transmitted from this first location to a second location via a hydraulic fluid, and the pressure is converted to a second mechanical effort at the second location. Thus, the hydraulic systems contemplated by the present invention include hydraulic brake systems, hydraulic steering mechanisms, hydraulic transmissions, hydraulic jacks and hydraulic lifts, especially those that require a high degree of fire resistance. Included among these are the hydraulic systems used in heavy equipment and transportation vehicles including highway and construction equipment, railways, planes and aquatic vehicles.

The heat transfer-type fluid systems include the hydraulic systems described above wherein heat is dissipated by the hydraulic fluid and include many other systems as well. In general, the present invention contemplates heat transfer systems wherein heat is passed from a first heat conductor at a first location to a heat transfer fluid, the heat is transmitted from the first location to a second location via the heat transfer fluid, and the heat is passed from the heat transfer fluid to a second conductor at the second location. Thus, the heat transfer systems of the present invention include heat dissipation systems, fluidic heating systems, e.g., radiator-type circulating fluid heating systems, heat exchange systems such as gas-liquid and liquid-liquid concurrent and countercurrent tubular heat exchangers as are used, for example, in the chemical process industries, cooling systems for nuclear reactors, radiator-type cooling systems, and any other temperature gradient systems in which a closed or sealed fluid heat transfer medium is used.

In the functional fluid systems of the present invention, the compounds of Formula I above are used in an effective amount. Thus, by an effective amount of these compounds is meant the compound product without additional fluid components as well as fluids containing additional fluid components. In one embodiment, the compounds of Formula I may be employed without additives or diluents. Alternatively, these compounds may comprise the base component of a functional fluid or may constitute a minor component, e.g., an additive, in a functional fluid containing a different base component. In general, an effective amount may be any amount which will produce the desired fluid characteristics for a given system. Therefore, as little as 5% or less of one or more of the compounds of Formula I may be used or as much as about 100% of the compounds may be used, percentages by weight. Preferably about 20% to about 95% of the functional fluid may be one or more of the compounds of Formula I; more preferably, about 45% to about 90% of the fluid may comprise one or more compounds of Formula I.

Various diluents, inhibitors and other additives are well known in the functional fluid art and these may optionally be added to the functional fluids used in the systems of the present invention, if desired.

Generally, the particular amount of diluents may widely vary. More particularly, the diluent components may constitute from 0 up to about 80% by weight of the fluid and preferably from about 20 to about 60%.

Various additives may be added to the fluids used in the systems of this invention to control or modify various chemicals and physical properties. Among the various types of additives which can be added to the fluids are included inhibitors for pH and corrosion control, antioxidants, rust inhibitors, viscosity index improvers, pour point depressants, lubricating additives, antifoamants, stabilizers, vapor phase corrosion inhibitors, rubber swelling adjusters, demulsifiers, dyes and odor suppressants. Generally, the total amount of additives which may be incorporated into the fluid composition will vary between 0 to about 20%, e.g., from about 0.1 to 8% and more specifically from about 0.2 to about 5% by weight based on the total weight of the fluid composition.

For example, alkaline inhibitors for pH and corrosion control may optionally be employed in an amount sufficient to maintain alkaline conditions in the fluid compositions, e.g., at an apparent pH value of from about 7 to about 11.5, if desired. These inhibitors may generally be added in an amount of from about 0 to about 8% by weight based on the total weight of fluid compositions, e.g., from about 0.5 to about 6%. Useful alkaline inhibitors include, for example, alkali metal salts of higher fatty acids such as potassium oleate, the potassium soap of rosin or tall oil fatty acids, amines such as morpholine and ethanolamine and amine salts such as mono- or dibutyl ammonium borates.

An antioxidant may optionally be used, if desired. Typical antioxidants include 2,2-di(4-hydroxyphenyl)-propane, phenothiazine, amines such as phenylalphanaphthylamine and hindered phenols such as dibutyl cresol. Generally, the amount of antioxidant used will vary from 0 to about 3% by weight, e.g., from about 0.001 to about 2% by weight based on the total weight of the fluid composition.

Additionally, other additives, if desired, may be incorporated into the fluid composition. For example, corrosion inhibitors such as butynediol and rubber swelling adjusters such as dodecyl benzene may be used.

The above-noted inhibitors and additives are merely exemplary and are not intended as an exclusive listing of the many well-known materials which can be added to fluid compositions to obtain various desired properties. Other illustrations of additives and diluents which may be used can be found in U.S. Pat. No. 3,377,288, and in *Introduction to Hydraulic Fluids* by Roger E. Hatton, Reinhold Publishing Corp. (1962).

The following examples depict various embodiments of the present invention; they are intended to be illustrative and not limiting in nature. All parts and percentages are by weight unless otherwise specified.

EXAMPLE 1

Preparation of Tris(2-Tri-Sec-Butoxysiloxyethyl)Isocyanurate: $C_3N_3O_3$—[$CH_2CH_2O$—$Si(OC_4H_9.sec)_3$]$_3$ A three-neck flask equipped with a condenser, thermometer, addition funnel and mechanical stirrer was charged with tris(2-hydroxyethyl)isocyanurate [136.0 grams (0.520 mole)], pyridine [136.9 grams (1.73 moles)] and toluene (600 milliliters). Then, tri-sec-butoxychlorosilane [468.7 grams (1.65 moles)] was added dropwise with stirring at room temperature (22° C.) over a period of two hours. The reaction mixture was then heated to 80° C. for three hours and then cooled to room temperature with continuous stirring. Solids were filtered and the organic phase of the filtrate was washed four times with 100 milliliters of distilled water for each wash. The aqueous phases after each washing were discarded and the resulting organic phase was dried over magnesium sulfate for twelve hours. After the toluene solvent and low boiling impurities were removed with simple distillation, a liquid product (162.8 grams) was obtained at 200° C. with molecular distillation. Product yield was 31.3% based on the moles of the tris(2-hydroxyethyl)isocyanurate employed.

Elemental analysis for $C_{45}H_{93}N_3O_{15}Si_3$: Calculated: C: 54.0% H: 9.37% N: 4.2% Si: 8.42%; Found: C: 53.9% H: 9.42% N: 4.0% Si: 9.14%.

EXAMPLE 2

Preparation of Tris(2-(4,4-Dimethyl-6,6,6-Tri-Sec-Butoxy)Disiloxyethyl)Isocyanurate: $C_3N_3O_3$—[$CH_2CH_2O$—$Si(CH_3)_2O$—$Si$—$(OC_4H_9.sec)_3$]$_3$ The procedure of Example 1 was repeated except the reaction vessel was charged with tris(2-hydroxyethyl)isocyanurate [76.2 grams (0.292 mole)], pyridine [87.5 grams (1.1 moles)] and toluene (300 milliliters). Then, 1-chloro-1,1-dimethyl-3,3,3-tri-sec-butoxydisiloxane [347.7 grams (0.973 mole)] was added dropwise at room temperature (20°-25° C.) over a period of 1.25 hours. Next, the reaction mixture was heated at 90° C. for 12 hours and then cooled to room temperature with constant stirring. The product work up was the same as described in Example 1. A liquid product (118.0 grams) was obtained by molecular distillation at 224° C. The product yield was 33% based on the tris(2-hydroxyethyl)isocyanurate reactant employed.

Elemental analysis for $C_{51}H_{111}N_3O_{18}Si_6$: Calculated: C: 50.1% H: 9.14% N: 2.44% Si: 13.8%; Found: C: 49.85% H: 8.88% N: 3.29% Si: 13.5%.

EXAMPLE 3

Preparation of Tris(2-(4,4,6,6-Tetramethyl-8,8,8-Tri-Sec-Butoxy)-Trisiloxyethyl)Isocyanurate: $C_3N_3O_3$—[$CH_2CH_2$—$(Si(CH_3)_2O)_2$—$Si(OC_4H_9.sec)_3$]$_3$ The procedure of Example 1 was repeated except the reaction vessel was charged with tris(2-hydroxyethyl)isocyanurate [75.7 grams (0.29 moles)], pyridine [75.7 grams (0.87 mole)] and toluene (350 milliliters) followed by the dropwise addition of 1-chloro-1,1,3,3-tetramethyl-5,5,5-tri-sec-butoxytrisiloxane [375.1 grams (0.87 mole)] with stirring at room temperature (20°-25° C.) over a period of three hours. The reaction mixture was then heated to 90° C. for five hours and then cooled to room temperature with continuous stirring. After the work up, the resulting product (96.0 grams) was obtained with molecular distillation. This product yield was 22% based on the moles of tris(2-hydroxyethyl)isocyanurate employed.

Elemental analysis for $C_{57}H_{129}N_3O_{21}Si_9$: Calculated: C: 47.4% H: 9.00% N: 2.90% Si: 17.5%; Found: C: 46.6% H: 8.81% N: 3.19% Si: 17.8%.

EXAMPLE 4

Preparation of
Tris[2-(4,4,6,6,8,8-Hexamethyl-10,10,10-Tri-Sec-Butoxytetrasiloxy)Ethyl]Isocyanurate:
$C_3N_3O_3$—[$CH_2CH_2O$—($Si(CH_3)_2O$)$_3$—$Si(OC_4H_9$-sec)$_3$]$_3$ The procedure of Example 1 was repeated except the reaction vessel was charged with tris(2-hydroxyethyl)isocyanurate [47.5 grams (0.18 mole)], pyridine [44.0 grams (0.56 mole)] and toluene (400 milliliters), followed by the dropwise addition of 1-chloro-1,1,3,3,5,5-hexamethyl-7,7,7-tri-sec-butoxytetrasiloxane with stirring at 23°–30° C. over a period of two hours. The reaction mixture was then heated to 85° C. for seven hours and then cooled to room temperature with continuous stirring. After employing a simple distillation step to remove solvent, the resulting product weighted 165 grams. The yield of this product was 54.9% based on the moles of tris(2-hydroxyethyl)isocyanurate employed.

Elemental analysis for $C_{63}H_{147}N_3O_{24}Si_{12}$: Calculated: C: 45.4% H: 8.88% N: 2.52% Si: 20.2%; Found: C: 45.2% H: 8.85% N: 2.30% Si: 20.9%.

EXAMPLE 5

Preparation of
Tris(2-(4,4,6,6,8,8,10,10-Octamethyl-12,12,12-Tri-Sec-Butoxypentasiloxy)Ethyl)Isocyanurate:
$C_3N_3O_3$—[$CH_2CH_2O$—($Si(CH_3)_2O$)$_4$—$Si(OC_4H_9$-sec)$_3$]$_3$ The procedure of Example 1 was repeated except the reaction vessel was charged with tris(2-hydroxyethyl)isocyanurate [66.4 grams (0.254 mole)], pyridine [69.8 grams (0.88 mole)] and toluene (350 milliliters), followed by the dropwise addition of 1-chloro-1,1,3,3,5,5,7,7-octamethyl-9,9,9-tri-sec-butoxypentasiloxane [441.6 grams (0.762 mole)] with stirring at 22° C. over a period of 2.5 hours. The reaction mixture was then heated to 85° C. for eight hours and then cooled to room temperature with continuous stirring. After the simple distillation step, the resulting product (276 grams) was not molecularly distillable. The yield of this product was 57.4% based on the moles of tris(2-hydroxyethyl)isocyanurate employed.

Elemental analysis for $C_{75}H_{165}N_3O_{27}Si_{15}$: Calculated: C: 43.8% H: 8.80% N: 2.22% Si: 22.3%; Found: C: 47.68% H: 8.82% N: 2.13% Si: 21.4%.

EXAMPLE 6

Preparation of
Tris(2-Trimethylsiloxyethyl)Isocyanurate:
$C_3N_3O_3$—[$CH_2CH_2O$—$Si(CH_3)_3$]$_3$ The procedure of Example 1 was repeated except the reaction vessel was charged with tris(2-hydroxyethyl)isocyanurate [89.7 grams (0.34 mole)], pyridine [81.5 grams (1.03 mole)] and toluene (500 milliliters), followed by the dropwise addition of trimethylchlorosilane [112.0 grams (1.03 mole)] at 50° C., with stirring over a period of 1.5 hours. Next, the reaction mixture was heated to 95° C. for 12 hours and then cooled to room temperature with constant stirring. The product workup was the same as in Example 1. A liquid product (129.7 grams) was obtained by vacuum distillation at 174°–177° C. The yield of this product was 79% based on the moles of tris(2-hydroxyethyl)isocyanurate employed.

Elemental analysis for $C_{18}H_{39}N_3O_6Si_3$: Calculated: C: 45.0% H: 8.0% N: 9.0% Si: 18%; Found: C: 47.42% H: 7.73% N: 9.43% Si: 19.1%.

EXAMPLE 7

Preparation of
Tris(2-Pentamethyl-Di-Siloxyethyl)Isocyanurate:
$C_3N_3O_3$—[$CH_2CH_2O$—$Si(CH_3)_2O$—$Si(CH_3)_3$]$_3$ The procedure of Example 1 was repeated except the reaction vessel was charged with tris(2-hydroxyethyl)isocyanurate [43.7 grams (0.167 mole)], pyridine [39.7 grams (0.502 mole)] and toluene (400 milliliters), followed by the dropwise addition of 1-chloro-1,1,3,3,3-pentamethyldisiloxane [91.6 grams (0.502 mole)] at 40° C., with stirring over a period of two hours. Next the reaction mixture was heated to 90° C. for two hours and then cooled to room temperature. The workup of the product was the same as described in Example 1. A liquid product (35.1 grams) was obtained by molecular distillation at 240° C. The yield of this product was 16.8% based on the moles of tris(2-hydroxyethyl)isocyanurate employed.

Elemental analysis for $C_{24}H_{57}N_3O_9Si_6$: Calculated: C: 41.2% H: 8.20% N: 6.00% Si: 24.0%; Found: C: 44.2% H: 7.49% N: 6.79% Si: 24.7%.

EXAMPLE 8

Preparation of
Tris(2-Heptamethyltrisiloxyethyl)Isocyanurate:
$C_3N_3O_3$—[$CH_2CH_2O$—($Si(CH_3)_2O$)$_2$—$Si(CH_3)_3$]$_3$ The procedure of Example 7 was repeated except the reaction vessel was charged with tris(2-hydroxyethyl)isocyanurate [39.2 grams (0.15 mole)], pyridine [39.4 grams (0.50 mole)] and toluene (600 milliliters), followed by the dropwise addition of 1-chloro-1,1,3,3,5,5,5-heptamethyltrisiloxane [116.9 grams (0.46 mole)] with stirring at 50° C. over a period of two hours. The reaction mixture was then heated to 90° C. for twelve hours and then cooled to room temperature (20°–25° C.) with continuous stirring. After workup, a liquid product (77.2 grams) was obtained by molecular distillation at 200° C. The yield of this product was 55.8% based on the moles of the tris(2-hydroxyethyl)isocyanurate employed.

Elemental analysis for $C_{30}N_{75}N_3O_{12}Si_9$: Calculated: C: 39.0% H: 8.00% N: 5.00% Si: 27.0%; Found: C: 39.94% H: 7.92% N: 4.78% Si: 28.2%.

EXAMPLE 9

Preparation of Tris(2-Nonamethyltetrasiloxyethyl) Isocyanurate:
$C_3N_3O_3$—[$CH_2CH_2O$—($Si(CH_3)_2O$)$_3$—$Si(CH_3)_3$]$_3$ The procedure of Example 7 was repeated except the reaction vessel was charged with tris(2-hydroxyethyl) isocyanurate [44.4 grams (0.17 mole)], pyridine [40.3 grams (0.51 mole)] and toluene (600 milliliters) followed by the dropwise addition of 1-chloro-1,1,3,3,5,5,7,7,7-nonamethyltetrasiloxane [168.7 grams (0.51 mole)] with stirring at 50° C. over a period of two hours. The reaction mixture was then heated to 90° C. for twelve hours and then cooled to room temperature with continuous stirring. After workup, the liquid product was obtained (134.3 grams) by molecular distillation at 200° C. The yield of this product was 71% based on the moles of tris(2-hydroxyethyl)isocyanurate employed.

Elemental analysis for $C_{36}H_{93}N_3O_{15}Si_{12}$: Calculated: C: 38.0% H: 8.00% N: 4.00% Si: 29.0%; Found: C: 37.7% H: 7.85% N: 3.90% Si: 32.8%.

EXAMPLE 10

Preparation of Tris (2-(4,4-Di-Sec-Butoxy-6,6,6-Trimethyl)Siloxyethyl-)Isocyanurate:

$C_3N_3O_3$—[$CH_2CH_2O$—$Si(OC_4H_9.sec)_2O$—$Si(CH_3)_3$]$_3$

The procedure of Example 7 was repeated except the reaction vessel was charged with tris(2-hydroxyethyl)isocyanurate [38.0 grams (0.15 mole)], pyridine [38.0 grams (0.48 mole)] and toluene (350 milliliters), followed by the dropwise addition of 1-chloro-1,1-di-sec-butoxy-3,3,3-trimethyldisiloxane [115.9 grams (0.44 mole)] with stirring at 45°–50° C. over a period of 2 hours. The reaction mixture was then heated to 90°–95° C. for eight hours and then cooled to room temperature with continuous stirring. After workup, a liquid product (54.2 grams) was obtained by molecular distillation at 245°–250° C. The yield of this product was 33.3% based on the moles of tris(2-hydroxyethyl)isocyanurate employed.

Elemental analysis for $C_{42}H_{93}N_3O_{15}Si_6$: Calculated: C: 46.2% H: 9.25% N: 4.15% Si: 16.6%; Found: C: 47.3% H: 8.64% N: 3.60% Si: 14.9%.

EXAMPLE 11

To demonstrate the lubricity and viscosity characteristics of the fluids, viscosities were determined by ASTM Method D-445 (1979), pour points were determined by ASTM Method D-97 (1979) and 4-Ball lubricity was determined by ASTM Method D-2266 (1979). The procedures of these three standard test methods were followed, except in the pour point test where the preliminary treatment cited in that test was excluded and only a solid $CO_2$/acetone bath was used. The Viscosity Index was calculated according to the standard formula.

The results are summarized in Table I.

TABLE I

| EXAMPLE | VISCOSITY 37.7° C. | VISCOSITY 98.8° C. | VISCOSITY INDEX | 4-BALL WEAR | POUR POINT (°C.) |
|---|---|---|---|---|---|
| 1 | 49.9 | 8.16 | 146 | .750 mm | −51 |
| 2 | 44.8 | 9.22 | 206 | .618 mm | −60 |
| 3 | 43.4 | 10.2 | 248 | .653 mm | −66 |
| 4 | 30.9 | 9.25 | 321 | 2.54 mm | −71 |
| 5 | 42.0 | 11.6 | 295 | 2.63 mm | −66 |
| 6 | 38.9 | 5.35 | 77.0 | 1.6 mm | −21 |
| 7 | 39.2 | 5.73 | 94.0 | 2.7 mm | −48 |
| 8 | 20.0 | 4.99 | 209 | 2.3 mm | −66 |
| 9 | 19.2 | 5.35 | 260 | 2.2 mm | −75 |
| 10 | 53.2 | 9.43 | 174 | .741 mm | −51 |

EXAMPLES 12-15

To demonstrate improvements in pour point depressions and viscosity index improvements in various base fluids, the products produced by Examples 1–10 were used as additives in three selected base fluids and the resulting properties of these base fluids with and without the additives were measured.

The results are summarized in Tables II, III and IV.

TABLE II

ADDITIVES IN A PHOSPHATE ESTER BASE FLUID[1]

| Example of Additive Compound | Amount of Additive Compound in Total Base Fluid Tested | $V_{37.7° C.}$ | $V_{98.8° C.}$ | Viscosity Index | Viscosity Index % Improvement | Pour Point | 4-Ball Wear | Lubricity % Improvement |
|---|---|---|---|---|---|---|---|---|
| — | 0% | 17.57 | 3.297 | 63 | — | −30° C. | .737 mm | — |
| 1 | 1% | 17.49 | 3.322 | 69 | 9.5% | −33° C. | .671 mm | 8.9% |
| 1 | 5% | 18.00 | 3.387 | 69 | 9.5% | −33° C. | .723 mm | 1.9% |
| 2 | 1% | 17.65 | 3.292 | 63 | 0 | −33° C. | .735 mm | .2% |
| 6 | 1% | 17.8 | 3.29 | 62 | −1.59% | −33° C. | .8808 mm | −19.5% |
| 7 | 1% | 17.8 | 3.31 | 64 | +1.59% | −33° C. | .8478 mm | −15.0% |
| 8 | 1% | 17.6 | 3.29 | 64 | +1.59% | −33° C. | .8516 mm | −11.5% |
| 9 | 1% | 17.6 | 3.32 | 67 | +4.76% | −33° C. | .8284 mm | −12.4% |

[1]FYRQUEL 90, a triaryl phosphate ester, produced by Stauffer Chemical Company, Specialty Chemical Division, Wesport, Connecticut, 06405.

TABLE III

ADDITIVES IN SELECTED FLUOROCARBON POLYMER BASE FLUID[2]

| Example of Additive Compound | Amount of Additive Compound in Total Base Fluid Tested | $V_{37.7° C.}$ | $V_{98.8° C.}$ | Viscosity Index | Viscosity Index % Improvement | Pour Point | 4-Ball Wear | Lubricity % Improvement |
|---|---|---|---|---|---|---|---|---|
| — | 0% | 310.5 | 10.86 | 11 | — | +6° C. | .741 mm | — |
| 1 | 1% | 297.3 | 11.49 | 18 | 63.6% | +6° C. | .543 mm | 26.7% |
| 1 | 5% | 235.6 | 10.71 | 24 | 118% | +3° C. | .764 mm | −3.1% |
| 2 | 1% | 287.4 | 10.67 | 13 | +18.8% | +3° C. | .612 mm | +17.3% |
| 6 | 5% | 259 | 10.0 | 12 | +9.09% | +6° C. | .6154 mm | +16.9% |
| 8 | 5% | 205 | 9.55 | 19 | +72.7% | +6° C. | .7729 mm | −4.35% |
| 9 | 5% | 193 | 9.54 | 23 | +109.1% | +3° C. | .7320 mm | +1.15% |

[2]FLONLUBE 900, a chlorotrifluoroethylene polymer having an average molecular weight of 900, produced by Asahi Glass Co., Ltd., 2-1-2 Marunouchi, Chiyoda-Ku, Tokyo, Japan.

TABLE IV

| | ADDITIVE IN SECOND FLUOROCARBON BASE FLUID[3] | | | | | | | |
|---|---|---|---|---|---|---|---|---|
| Example of Additive Compound | Amount of Additive Compound in Total Base Fluid Tested | $V_{37.7° C.}$ | $V_{98.8° C.}$ | Viscosity Index | Viscosity Index % Improvement | Pour Point | 4-Ball Wear | Lubricity % Improvement |
| — | 0% | 20.3 | 2.89 | 9 | — | −39° C. | .6737 mm | — |
| 6 | 1% | 20.4 | 2.91 | 10 | +11.1% | −39° C. | .5989 mm | +11.1% |
| 7 | 1% | 20.6 | 2.89 | 8 | −11.1% | −39° C. | .6446 mm | +4.32% |
| 8 | 1% | 20.1 | 2.92 | 13 | +44.4% | −39° C. | .6527 mm | +3.12% |
| 9 | 1% | 20.0 | 2.91 | 12 | +33.3% | −39° C. | .6883 mm | −2.17% |

[3]FLONLUBE 700, a chlorotrifluoroethylene polymer having an average molecular weight of 700, produced by Asahi Glass Co., Ltd., 2-1-2 Marunouchi, Chiyoda-Ku, Tokyo, Japan.

What is claimed is:

1. A compound of the formula:

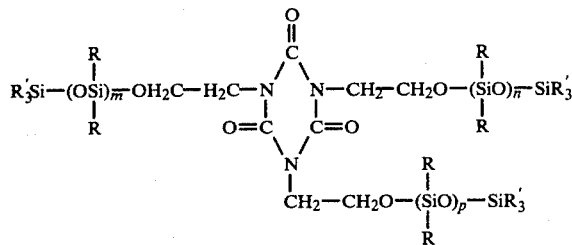

wherein each R and R′ is individually selected from lower alkyl groups having 1 to 4 carbon atoms and lower alkoxy groups having 1 to 4 carbon atoms; and the sum of m, n and p is from 0 to about 20; with the proviso that R′ is a lower alkoxy group when the sum of m, n, and p is 0.

2. The compound of claim 1 wherein each R is the same.

3. The compound of claim 1 wherein each R′ is the same.

4. The compound of claim 3 wherein each R′ is a lower alkoxy group having 1 to 4 carbon atoms.

5. The compound of claim 4 wherein each R′ is a sec-butoxy group.

6. The compound of claim 2 wherein the sum of m, n, and p is from 0 to about 12.

* * * * *